(12) United States Patent
Krasnoff

(10) Patent No.: US 12,201,552 B2
(45) Date of Patent: *Jan. 21, 2025

(54) URETHRA CONDOM AND KIT HAVING THE SAME

(71) Applicant: Duplicent, LLC, Santa Monica, CA (US)

(72) Inventor: Curren Emmett Krasnoff, Santa Monica, CA (US)

(73) Assignee: Duplicent, LLC, Santa Monica, CA (US)

( * ) Notice: Subject to any disclaimer, the term of this patent is extended or adjusted under 35 U.S.C. 154(b) by 431 days.

This patent is subject to a terminal disclaimer.

(21) Appl. No.: 17/737,165

(22) Filed: May 5, 2022

(65) Prior Publication Data

US 2023/0355427 A1 Nov. 9, 2023

Related U.S. Application Data

(63) Continuation of application No. 17/502,604, filed on Oct. 15, 2021, now Pat. No. 11,331,212, which is a continuation of application No. PCT/US2021/034955, filed on May 28, 2021.

(60) Provisional application No. 63/179,259, filed on Apr. 24, 2021.

(51) Int. Cl.
*A61F 6/04* (2006.01)

(52) U.S. Cl.
CPC .......... *A61F 6/04* (2013.01); *A61F 2006/047* (2013.01)

(58) Field of Classification Search
CPC ........ A61F 6/04; A61F 2006/048; A61F 5/41; A61F 2005/414; A61F 2006/041; A61F 6/005; A61F 6/146; A61F 6/00; A61F 6/065; A61F 6/02; A61F 2005/411; A61F 5/453; A61F 6/06; A61F 13/471; A61F 13/82; Y10S 128/918

See application file for complete search history.

(56) References Cited

U.S. PATENT DOCUMENTS

| | | | |
|---|---|---|---|
| 3,677,225 A * | 7/1972 | Czirely | A61F 6/04 604/352 |
| 4,821,742 A * | 4/1989 | Phelps, III | A61F 6/04 128/842 |
| 6,035,854 A | 3/2000 | Blake | |
| 6,145,507 A | 11/2000 | Hardy | |
| 6,148,819 A | 11/2000 | Winkler | |

(Continued)

FOREIGN PATENT DOCUMENTS

| | | | |
|---|---|---|---|
| GB | 1 595 911 A | 8/1981 | |
| GB | 1595711 A * | 8/1981 | ............... A61F 6/04 |

OTHER PUBLICATIONS

Detachol Adhesive Remover, published on WoundSource, dated Apr. 25, 2020, 3 pages.

(Continued)

*Primary Examiner* — Ophelia A Hawthorne

(74) *Attorney, Agent, or Firm* — GREENBERG TRAURIG, LLP

(57) ABSTRACT

A condom product includes a condom. The condom includes a body having an interior surface, an exterior surface, a distal end, and a proximal end having a peripheral edge. The condom is sized such that the interior surface is configured to extend along at least a portion of a head of a penis, but not along a shaft of the penis.

18 Claims, 11 Drawing Sheets

(56) References Cited

U.S. PATENT DOCUMENTS

| | | | |
|---|---|---|---|
| 11,331,212 B1* | 5/2022 | Krasnoff | ............... A61F 6/005 |
| 2007/0175484 A1 | 8/2007 | Staab | |
| 2014/0076329 A1* | 3/2014 | Rhodes | ................. A61F 6/04 |
| | | | 128/844 |
| 2016/0331578 A1* | 11/2016 | Sumina | ................. A61F 6/04 |

OTHER PUBLICATIONS

International Search Report and Written Opinion for International Application No. PCT/US2021/034955, mailed Oct. 6, 2021, 13 pages.

* cited by examiner

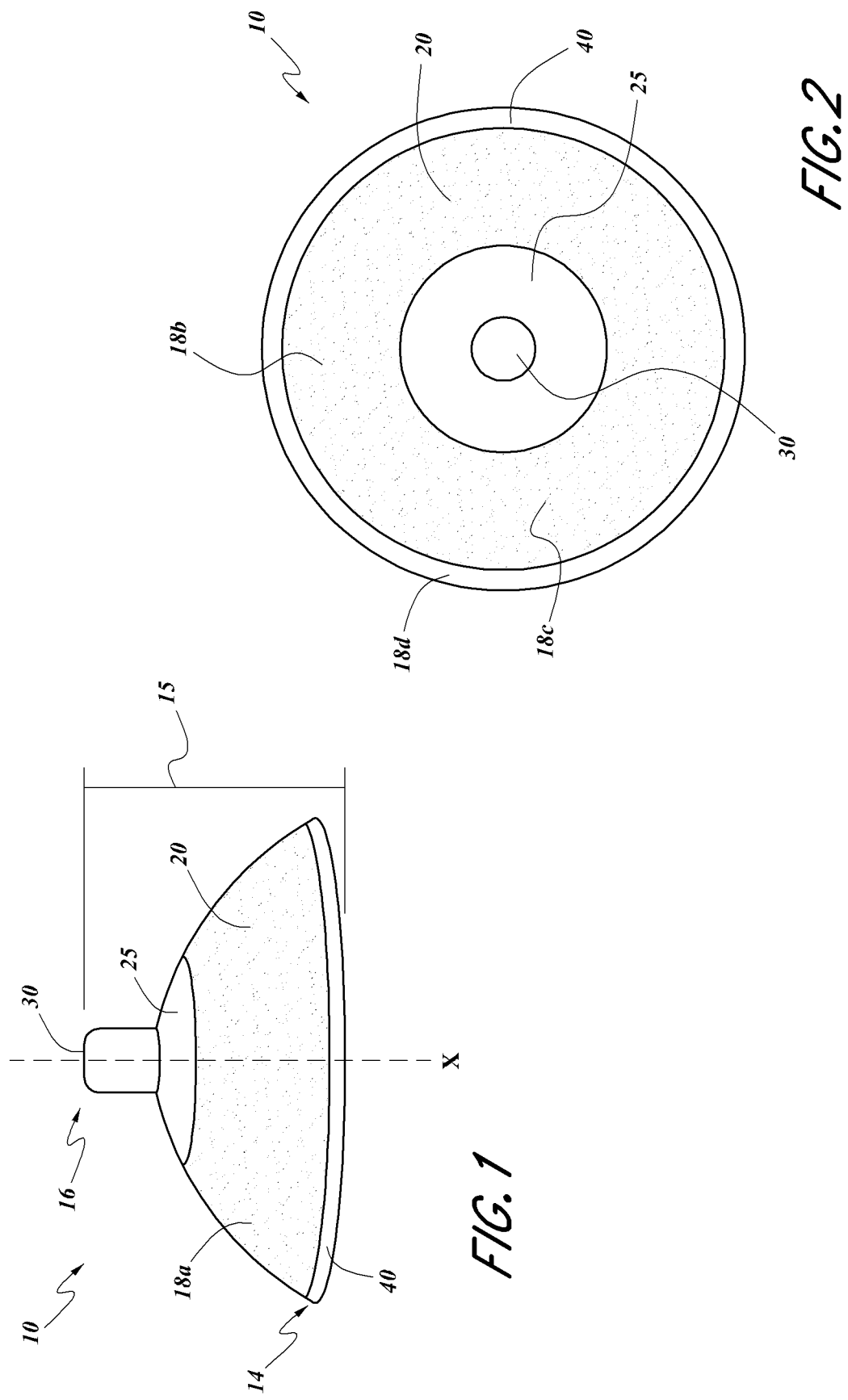

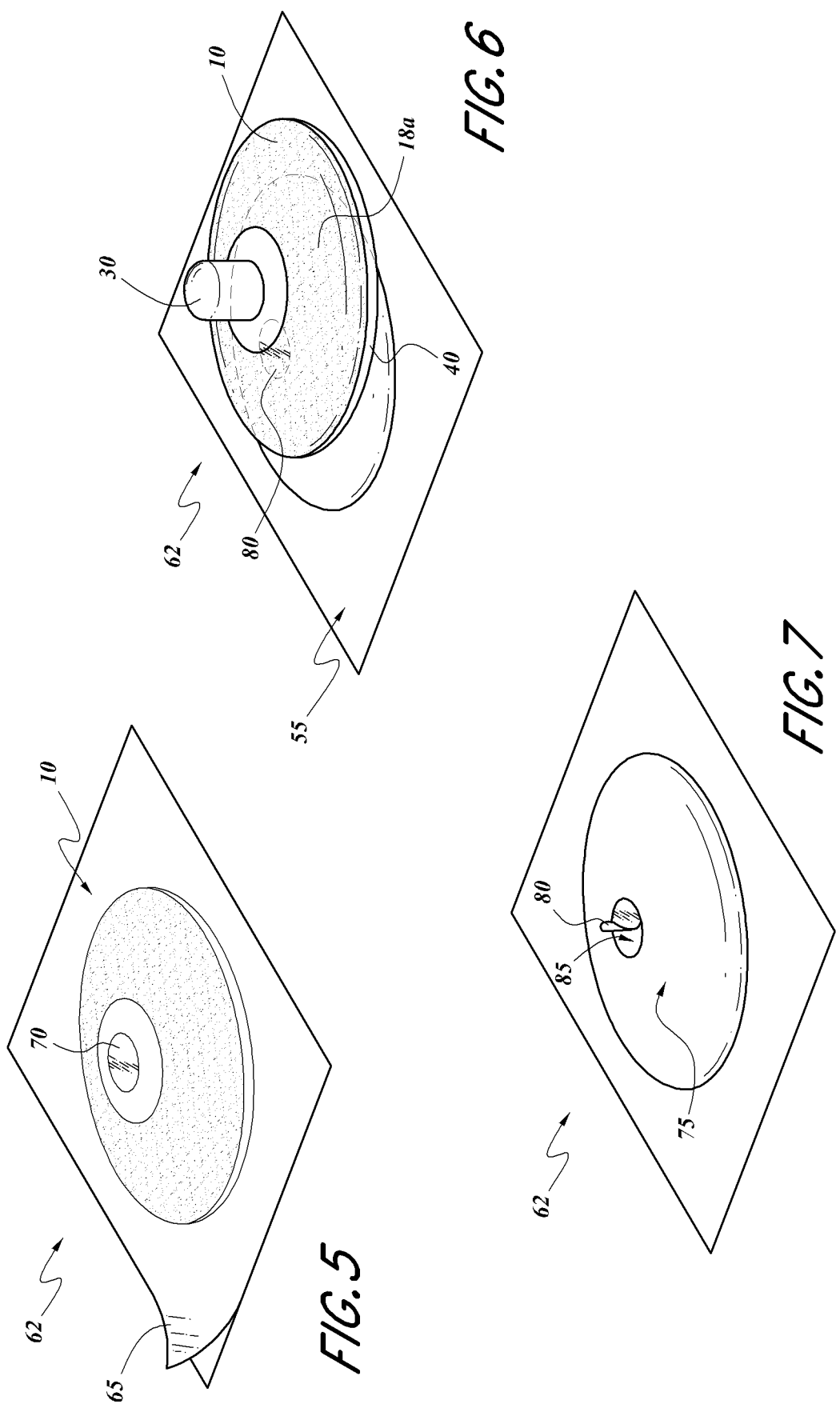

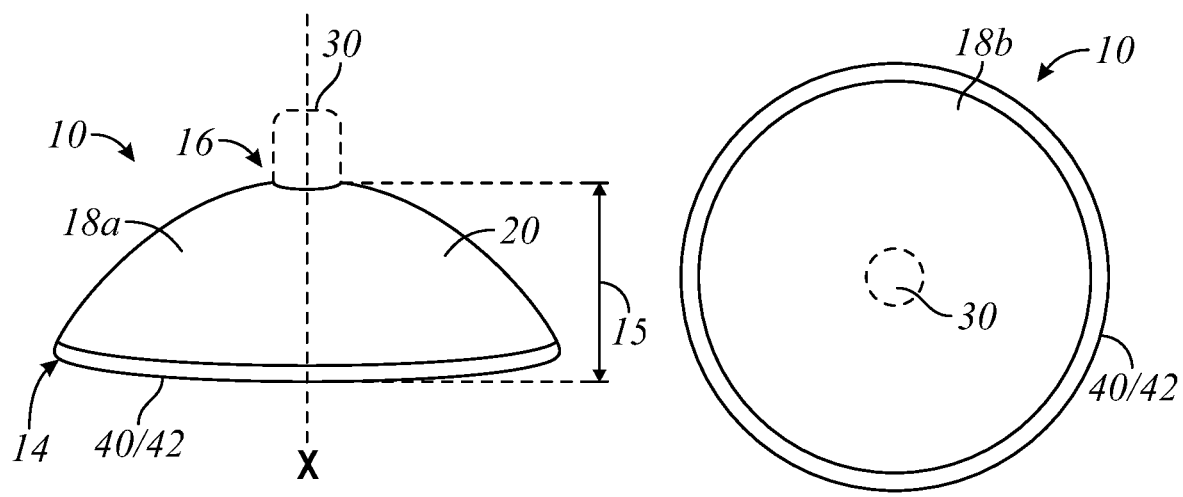
FIG. 22  FIG. 23
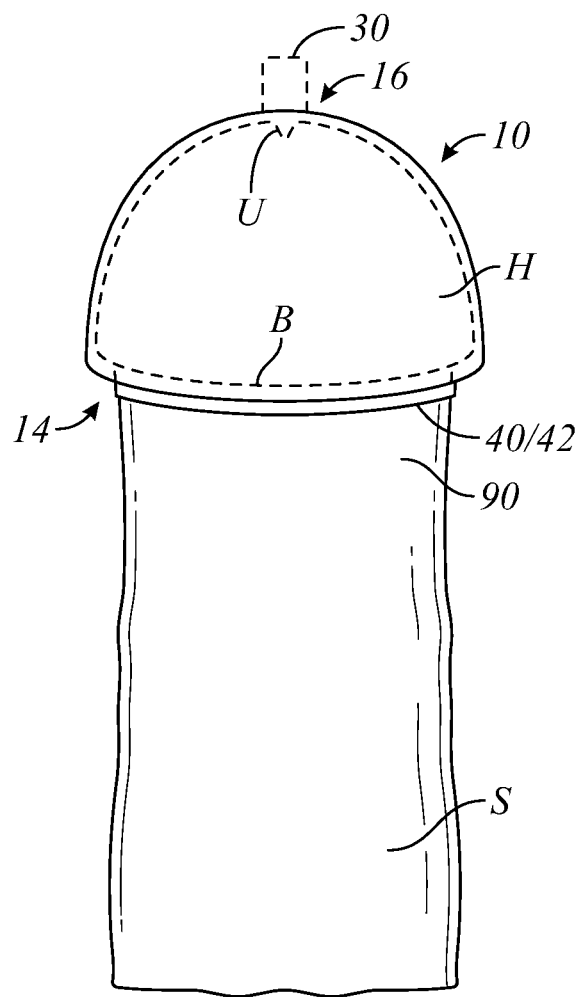
FIG. 24

URETHRA CONDOM AND KIT HAVING THE SAME

CROSS-REFERENCE TO RELATED PATENT APPLICATIONS

This application is a continuation of U.S. patent application Ser. No. 17/502,604, filed Oct. 15, 2021, which is a continuation of International Patent Application No. PCT/US2021/034955, filed May 28, 2021, which claims the benefit of and priority to U.S. Provisional Patent Application No. 63/179,259, filed Apr. 24, 2021, all of which are incorporated herein by reference in their entireties.

FIELD

The present disclosure is directed to contraceptive devices, and more particularly to a urethra condom for use during sexual intercourse, and a kit having the same.

BACKGROUND

Condoms have long been used to reduce the probability of pregnancy and spreading sexually transmitted diseases during sexual intercourse. Conventional condoms cover the head and shaft of the male penis. One drawback with conventional condoms is that users can experience a loss of the natural sensation or feeling during use, making sexual intercourse less pleasurable. Condoms with textured features (e.g., studded, ribbed) have been used to try to provide an improved sensation or feel during use, but these have also proved ineffective in providing the natural sensation of sexual intercourse without a condom.

SUMMARY

There is a need for an improved condom design that can provide the contraceptive and barrier to sexually transmitted diseases, while providing for improved feel or sensation during sexual intercourse.

One embodiment relates to a condom product. The condom product includes a condom. The condom includes a body having an interior surface, an exterior surface, a distal end, and a proximal end having a peripheral edge. The condom is sized such that the interior surface is configured to extend along at least a portion of a head of a penis, but not along a shaft of the penis.

In some embodiments, the condom includes an adhesive disposed along at least a portion of the interior surface.

In some embodiments, the adhesive is not positioned at the distal end.

In some embodiments, the distal end comprises a first material having a first flexibility or elasticity and the portion having the adhesive disposed thereon comprises as a second material having a second flexibility or elasticity that is less than the first flexibility or elasticity.

In some embodiments, the adhesive is positioned at the distal end, and the adhesive at the distal end is configured to at least partially close a urethra opening of the penis.

In some embodiments, the adhesive is not positioned proximate the peripheral edge, thereby defining a ring that does not include the adhesive along the inner surface adjacent the peripheral edge.

In some embodiments, the adhesive is positioned proximate the peripheral edge and extends at least partially along the interior surface toward the distal end to define an adhesive strip around at least a lower portion of the inner surface proximate the proximal end.

In some embodiments, the condom includes a removable liner disposed over the portion of the interior surface having the adhesive disposed thereon.

In some embodiments, the condom includes a reservoir extending from the distal end of the body.

In some embodiments, the reservoir is expandable.

In some embodiments, the reservoir is semi-rigid or rigid.

In some embodiments, the condom includes an elastic band positioned at the peripheral edge. The elastic band is configured to at least partially secure the condom to the head of the penis.

In some embodiments, the condom is sized such that the elastic band is configured to engage with a base of the head of the penis.

In some embodiments, the body comprises a material that permits the body to stretch around and squeeze against the portion of the head of the penis to (i) at least partially secure the condom to the head of the penis and (ii) at least partially close the urethra opening of the penis.

In some embodiments, the condom is dissolvable when exposed to water above a threshold temperature.

In some embodiments, the condom product includes an adhesive remover.

In some embodiments, the condom is stored in a first package and the adhesive remover is stored in a second package.

In some embodiments, the condom product includes a container that co-packages the first package and the second package.

In some embodiments, the container co-packages a plurality of the first packages and one or more of the second packages.

In some embodiments, the condom product includes a package. The package includes a base, an adhesive remover reservoir disposed along the base with the condom stacked on top of the adhesive remover reservoir, and a removable cover coupled to the base and extending over the adhesive remover reservoir and the condom. The adhesive remover is stored within the adhesive remover reservoir.

In some embodiments, the condom product includes a plurality of the packages detachably coupled to one another.

Another embodiment relates to a urethra condom. The urethra condom includes a piece of flexible natural or synthetic material (e.g., latex, polyurethane, lambskin, etc.) that is adhesively secured over the urethra to a portion of the head of the male penis for the purpose of preventing exchange of bodily fluids from the male urethra during sexual intercourse. The urethra condom ("penis cap" or "cap") covers a portion of the penis head, specifically, the urethra and area surrounding the urethra. The cap is formed in a concave dome to fit to the penis head with a topical skin adhesive (e.g., epidermal adhesive) formed on one side of the cap (the concave side that faces the penis), to adhesively secure the cap temporarily to the penis head and to prevent the exchange of fluids between the urethra and the vagina or other sexual orifice. The urethra condom has the practical medical and commercial use as birth control and prevention material for some sexually transmitted diseases and viruses.

Another embodiment relates to a urethra condom. The urethra condom includes a body extending between a rim at a proximal end and a reservoir tip at a distal end. The body has an outer convex surface extending between the rim and the reservoir tip and an inner concave surface configured to contact at least a portion of a head of a penis when the condom is applied thereto. The body has a height between the proximal end and the distal end such that, when the urethra condom is disposed on the penis, the rim at the proximal end of the body is disposed above the bottom edge of a head of the penis. At least a portion of the inner concave surface of the urethra condom has an adhesive disposed thereon configured to removably adhere the body of the urethra condom to the head of the penis when the urethra condom is disposed on the penis.

Another embodiment relates to a condom kit or product. The kit or product includes one or more urethra condoms, an adhesive remover, and a package removably housing the one or more urethra condoms and the adhesive remover. Each of the one or more urethra condoms includes a body extending between a rim at a proximal end thereof and a reservoir tip at a distal end thereof. The body has an outer convex surface extending between the rim and the reservoir tip and an inner concave surface configured to contact at least a portion of a head of a penis when the urethra condom is applied thereto. The body has a height between the proximal end and the distal end such that, when the urethra condom is disposed on the penis, the rim at the proximal end of the body is disposed above the bottom edge of the head of the penis. At least a portion of the inner concave surface has an adhesive disposed thereon configured to removably adhere the body to the head of the penis when the condom is disposed on the penis. The adhesive remover is configured for application by the user to the concave inner surface of the body such that the adhesive remover contacts the adhesive on the concave inner surface to thereby deactivate the adhesive to allow the removal of the urethra condom from the head of the penis.

Another embodiment relates to a method for removing a urethra condom from a penis.

The urethra condom has a body extending between a rim at a proximal end thereof and a reservoir tip at a distal end thereof. The body has an outer convex surface extending between the rim and the reservoir tip and an inner concave surface configured to contact at least a portion of a head of the penis when the urethra condom is applied thereto. The body has a height between the proximal end and the distal end such that, when the condom is disposed on the penis, the rim at the proximal end of the body is disposed above the bottom edge of the head of the penis. At least a portion of the inner concave surface has an adhesive disposed thereon configured to removably adhere the body to the head of the penis when the urethra condom is disposed on the penis. The method comprises lifting an edge of the rim at the proximal end of the body, delivering an adhesive remover under the edge of the rim so that the adhesive remover contacts the adhesive on the concave inner surface of the body to thereby deactivate the adhesive, and removing the body from on top of the head of the penis.

Another embodiment relates to a method for removing a condom from a penis. The condom is made of a dissolvable material (e.g., polyvinyl alcohol, solvent soluble polymer, etc.).

The method comprises exposing the condom (e.g., following use of the condom in sexual intercourse) to a dissolving agent (e.g., liquid, gel, spray) or water at a predetermined temperature (e.g., while in the shower, bath, etc.), so that the dissolving agent initiates, facilitates, or causes the dissolving of the condom.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE DRAWINGS

FIG. 1 is a top perspective view of a condom, according to an exemplary embodiment.

FIG. 2 is a bottom view of the condom of FIG. 1, according to an exemplary embodiment.

FIG. 5 is a top perspective view of an individual package of the kit of FIG. 3 showing the packaging partially opened, according to an exemplary embodiment.

FIG. 6 is a top perspective view of the individual package of FIG. 5 with a cover of the packaging removed and the condom partially removed from the packaging, according to an exemplary embodiment.

FIG. 7 is a top perspective view of a base of the individual package of FIG. 5 with a seal of an adhesive remover cavity partially detached to expose the adhesive remover cavity containing adhesive remover after the condom has been fully removed from the packaging, according to an exemplary embodiment.

FIG. 22 is a top perspective view of a condom, according to yet another exemplary embodiment.

FIG. 23 is a bottom view of the condom of FIG. 22, according to an exemplary embodiment.

FIG. 24 shows the condom of FIG. 22 in place over a head of a penis, according to an exemplary embodiment.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Figure 8:
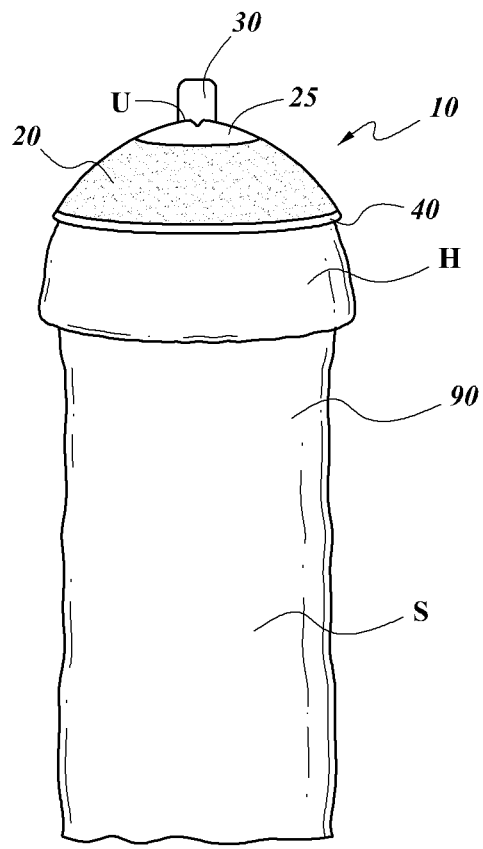
FIG. 8 shows the condom of FIG. 1 in place on a head of a penis prior to ejaculation, according to an exemplary embodiment.
Figure 9:
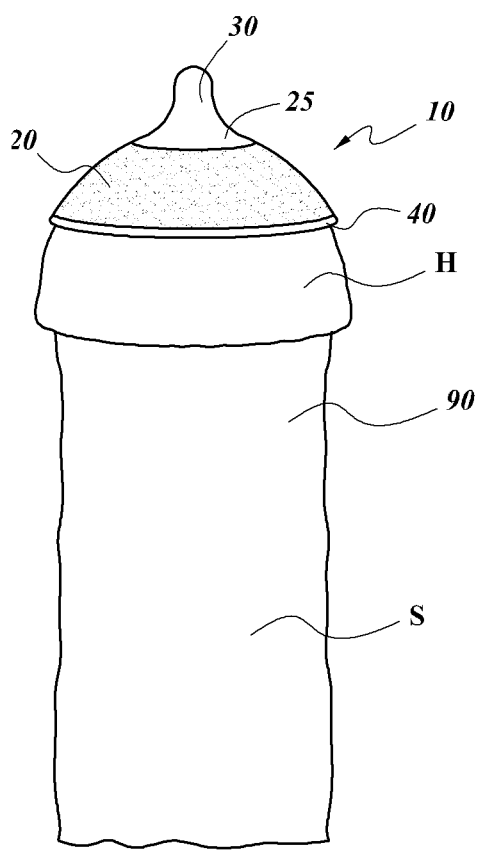
FIG. 9 shows the condom of FIG. 1 in place on a head of a penis after ejaculation with the condom trapping the ejaculated semen therein, according to an exemplary embodiment.
Figure 10:
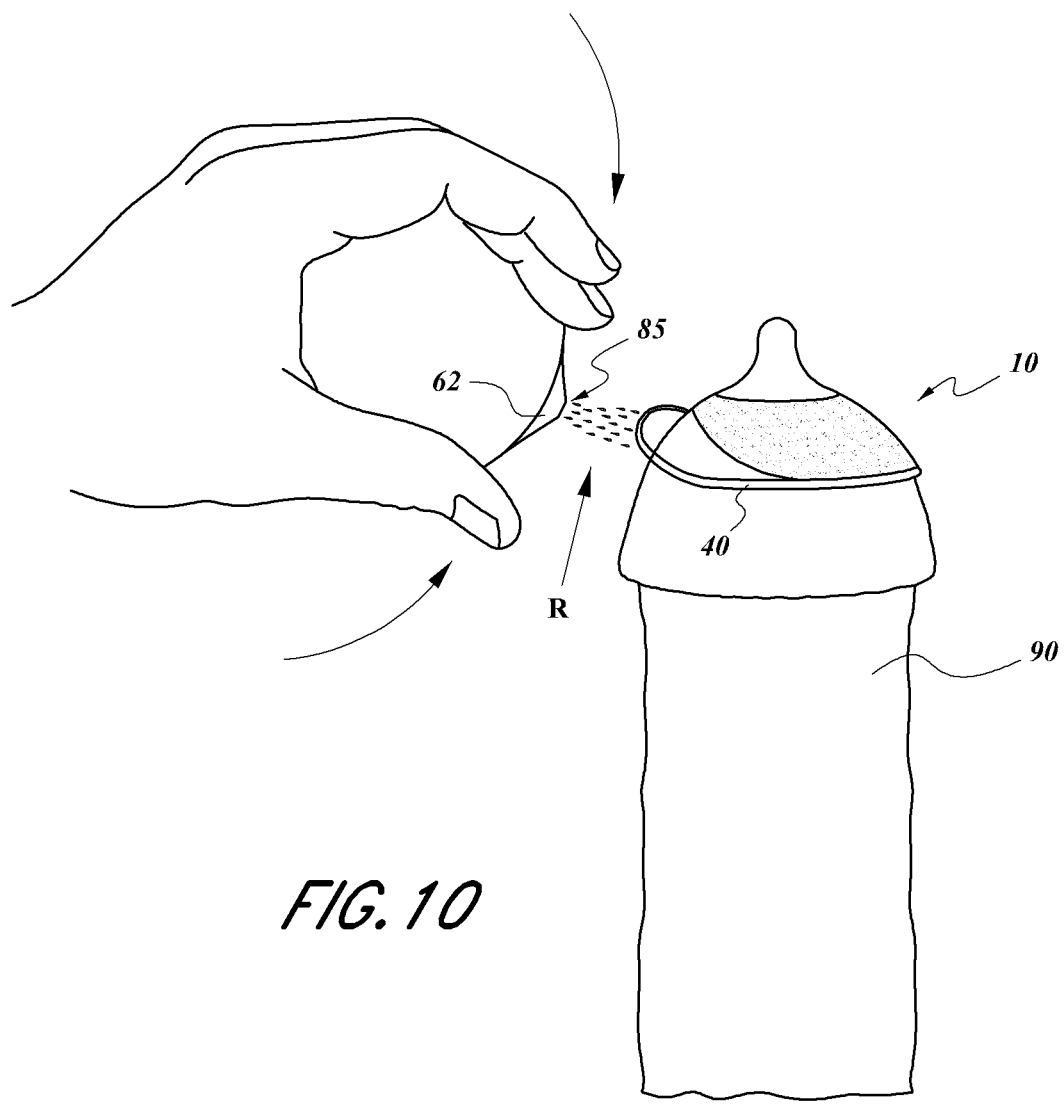
FIG. 10 shows the condom of FIG. 9 partially removed from the head of the penis upon application of an adhesive remover to the condom, according to an exemplary embodiment.

As shown in FIGS. 1 and 2, a penis cap or urethra condom, shown as condom 10, has a main body portion or body that extends from a lower circumferential/peripheral edge, shown as rim 40, at a base, shown as proximal end 14, to a tip, shown as distal end 16. The body of the condom 10 has an outer surface, shown as outer convex surface 18a, and an inner surface, shown as inner concave surface 18b. While the body is shown as having a convex dome shape, in other embodiments, the condom 10 is substantially flat (e.g., a circle disc shape) and forms to the shape of the head H of the penis 90 of the user upon application. In use, as shown in FIGS. 8-10, the inner concave surface 18b is disposed against at least a portion of the head H of the penis 90. In one embodiment, the condom 10 is configured to cover less than the entire head H of the penis 90 and does not cover or extend onto the shaft S of the penis 90 (e.g., the condom 10 may have a height 15 between the proximal end 14 and the distal end 16 so that the condom 10 does not extend to the bottom of the head H of the penis 90, and therefore does not extend below the head H of the penis 90 onto the shaft S). In another embodiment, the condom 10 is configured to cover the entire head H of the penis 90, but does not cover or extend onto the shaft S of the penis 90 (e.g., the condom 10 may have a height 15 between the proximal end 14 and the distal end 16 so that the condom 10 extends to the bottom of the head H of the penis 90, but does not extend below the head H of the penis 90). In various embodiments, the condom 10 is configured to cover 90% or less, 80% or less, 60% or less, 50% or less, 40% or less, or 30% or less of the head H of the penis 90. However, in other embodiments, the condom 10 can have other dimensions than the values noted above so that the condom 10 covers more or less of the head H of the penis 90, while not covering the shaft S of the penis 90. In some embodiments, the condom 10 is very small and is configured to cover only the urethra opening U and area directly surrounding the urethra opening U (e.g., covering approximately 20-35% of the entire head H of the penis 90).

As shown in FIGS. 1 and 2, the condom 10 has a receptacle, shown as reservoir 30, positioned at the tip of the distal end 16 for receiving or trapping semen during or following sexual intercourse. According to an exemplary embodiment, the reservoir 30 is manufactured from a flexible or expandable material (e.g., a material that is used to make traditional condoms, latex, polyurethane, polyisoprene, lamb intestine, etc.). In one embodiment, the reservoir 30, when expanded, is a generally cylindrical tip adjacent the outer convex surface 18a and defines the distal tip of the condom 10. In other embodiments, the condom 10 does not include the reservoir 30 (see, e.g., FIGS. 16-21) or the reservoir 30 is otherwise shaped when filled with semen (e.g., balloon shaped, etc.). In still other embodiment, the reservoir 30 is manufactured from a non-flexible or non-expandable material (e.g., semi-rigid plastics, rigid plastics, etc.).

As shown in FIG. 2, at least a portion 18c of the inner concave surface 18b has an adhesive 20 disposed thereon. In other embodiments, the inner concave surface 18b does not include the adhesive 20 (e.g., the condom 10 has a "stretch fit" or "tensioned" design). As shown in FIG. 2, (i) the inner concave surface 18b has a ring 18d extending around the rim 40 at the proximal end 14 of the condom 10 that does not have the adhesive 20 disposed thereon and (ii) the inner concave surface 18b has a circumferential gap 25 between the reservoir 30 and the portion 18c where the circumferential gap 25 does not have the adhesive 20 disposed thereon.

While the ring 18d is shown as extending around the entire circumference/perimeter of the proximal end 14, in some embodiments, only a portion of the ring 18d does not include the adhesive 20 (i.e., the adhesive 20 is at least partially disposed about the ring 18d). By way of example, the portion of the ring 18d that does not include the adhesive 20 may be between 5-50% of the circumference/perimeter of the proximal end 14 of the condom 10. In other embodiments, the condom 10 does not include the ring 18d such that the adhesive 20 extends to the rim 40 at the proximal end 14 of the condom 10. In an alternative embodiment, only the ring 18d has the adhesive 20 disposed thereon (e.g., forming an adhesive strip perimeter), while the remainder of the inner concave surface 18b does not include the adhesive 20. According to an exemplary embodiment, the diameter of the circumferential gap 25 is greater than the urethra opening U over which the condom 10 is placed during use. In some embodiments, the cross-sectional diameter of the reservoir 30 (e.g., along a plane transverse to the axis X of the condom 10) is greater than the urethra opening U over which the condom 10 is placed during use.

Figure 3:
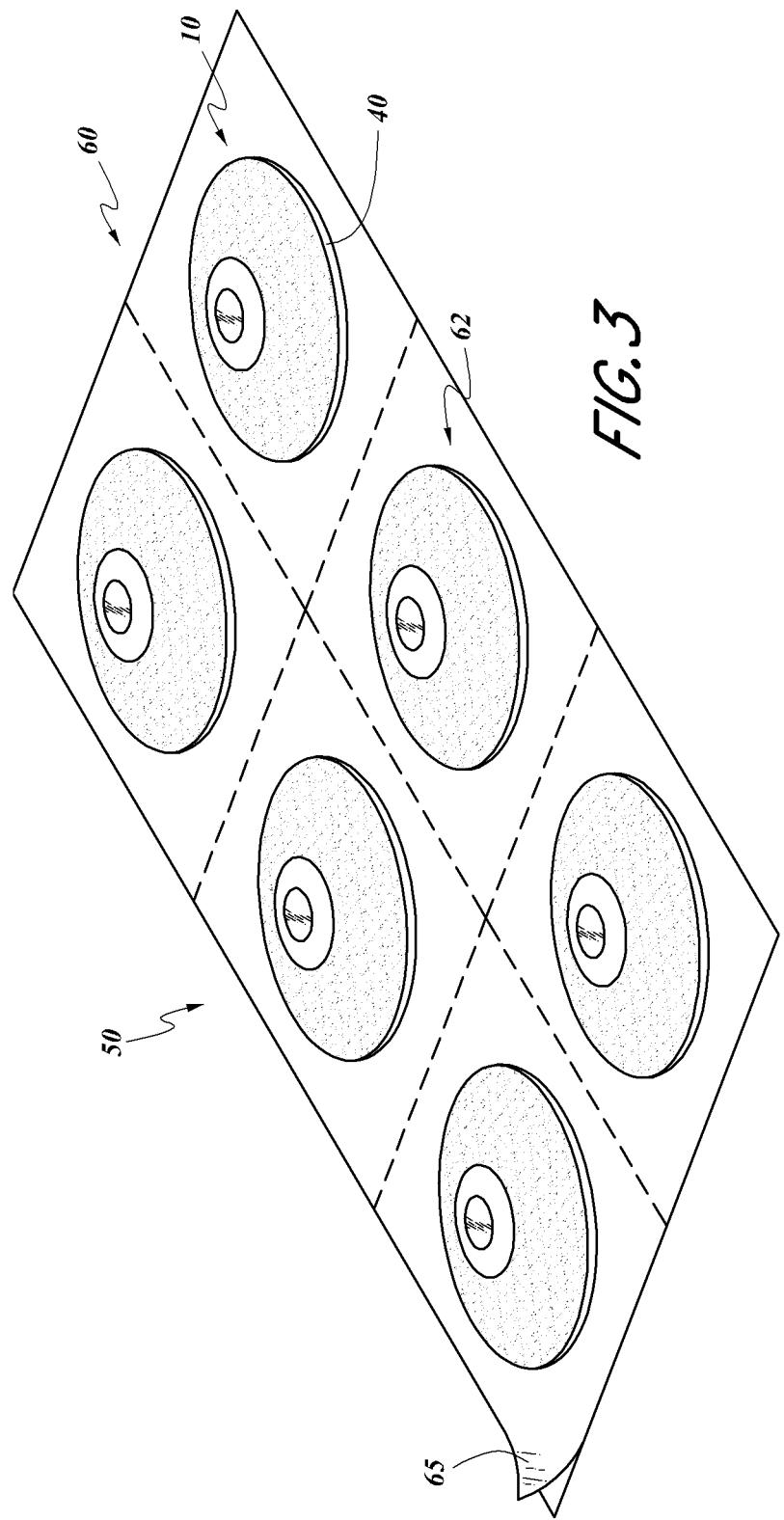
FIG. 3 is a top perspective view of a kit including a plurality of the condoms of FIG. 1, according to an exemplary embodiment.
Figure 4:
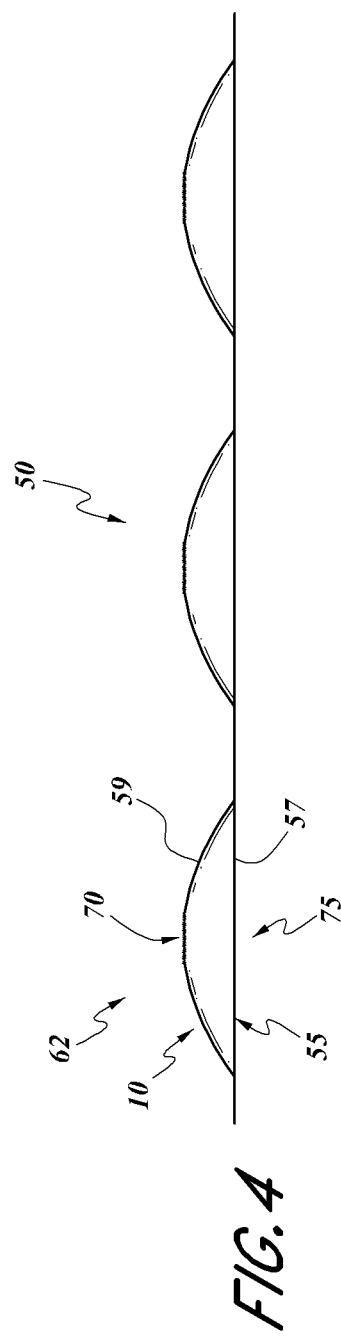
FIG. 4 is a side view of the kit of FIG. 3, according to an exemplary embodiment.

As shown in FIGS. 3 and 4, a plurality of the condoms 10 can be provided together in a condom product or kit. The kit includes packaging (e.g., disposable packaging, biodegradable packaging, etc.), shown as sheet package 50, having a base layer, shown as base 55, and a top layer, shown as removable cover 65, with the condoms 10 disposed between the base 55 and the removable cover 65. As shown in FIG. 4, the reservoir 30 of each of the condoms 10 (if the condoms 10 include the reservoir 30) is in a collapsed configuration 70 when the condoms 10 are disposed within the sheet package 50. As shown in FIG. 3, the sheet package 50 can be scored or perforated along separation lines 60 to allow individual condom packages 62 to be detached or otherwise removed from the sheet package 50 (see, e.g., FIGS. 5-7). Such scoring or perforations can be provided using a laser scoring process or a mechanical cutting process.

However, other suitable mechanisms for providing the separation lines 60 on the sheet package 50 can be used. In other embodiments, another suitable method, other than scoring, can be used to allow individual disposable condom packages 62 to be detached, torn off, or broken off from the sheet package 50. For example, in another embodiment, the sheet package 50 can include frangible portions between the individual disposable condom packages 62, where the frangible portions can break or tear to allow the individual disposable condom packages 62 to be detached from the sheet package 50 (e.g., when a user bends the sheet package 50 about the frangible portion to detach an individual disposable condom package 62). In an alternative embodiment, the kit can include a plurality of separate individual disposable condom packages 62 in a container (e.g., a box), where the user can simply remove each of the separate individual disposable condom packages 62 from the container individually.

As shown in FIGS. 4, 6, and 7, the base 55 of the sheet package 50 has a bottom layer 57 and a reservoir or dome portion 59 extending from the bottom layer 57 in each of the individual disposable condom packages 62. The bottom layer 57 can, in one embodiment, be generally planar (e.g., flat). The dome portion 59 can, in one embodiment, be a convex surface.

In another embodiment, the dome portion 59 can be defined by a pyramid like surface. As shown in FIGS. 4 and 7, the dome portion 59 and the bottom layer 57 define a compartment, shown as adhesive remover cavity 75, therebetween that releasably holds an amount of an adhesive remover R, as further discussed below. The internal volume of the adhesive remover cavity 75 of each of the individual disposable condom packages 62 can be filled with the adhesive remover R to the edges of each individual disposable condom package 62 (e.g., like a pocket), where the top (e.g., dome portion 59) and bottom (e.g., bottom layer 57) of the individual disposable condom package 62 can be flexible to allow squeezing of the adhesive remover cavity 75 to deliver the adhesive remover R to a desired location (e.g., onto the condom 10, under the condom 10, onto the head H of the penis 90, etc.).

As shown in FIGS. 6 and 7, the adhesive remover cavity 75 of each of the individual disposable condom packages 62 of the sheet package 50 can have an aperture, shown as adhesive opening 85, at the top of the dome portion 59 that is releasably sealed with a removable cover, shown as seal 80. The seal 80 can be secured over the adhesive opening 85 with an adhesive or bonded (e.g., with heat) to the dome portion 59. The seal 80 can be manually removed by the user to allow the delivery of the adhesive remover R from the adhesive remover cavity 75. In another embodiment, the seal 80 can be punctured to allow access to the adhesive remover R in the adhesive remover cavity 75. According to an exemplary embodiment, the seal 80 provides a water/air tight seal to the adhesive remover cavity 75.

During manufacture of the sheet package 50, the adhesive remover cavity 75 can be filled with the adhesive remover R, the adhesive opening 85 can be sealed with the seal 80, the condom 10 can be disposed over each of the dome portions 59 of the sheet package 50 (e.g., with the reservoir 30 of the condom 10 in the collapsed configuration 70), and the removable cover 65 can be disposed over and coupled to the bottom layer 57 of the sheet package 50 (e.g., with an adhesive, using a heating process, etc.), thereby, securing the condoms 10 over the dome portions 59 and within the sheet package 50. The separation lines 60 may, thereafter, be formed in the sheet package 50 to generate the individual disposable condom packages 62 connected by the separation lines 60. Alternatively, the sheet package 50 may be separated such that the individual disposable condom packages 62 are pre-separated, which can then be inserted into a container or box.

As shown in FIGS. 5-7, the individual disposable condom package 62 is depicted in various stages during use. In FIG. 5, the removable cover 65 is in the process of being detached from the bottom layer 57 to allow access to the condom 10. In FIG. 6, the removable cover 65 has been removed and the condom 10 is being removed from on top of the dome portion 59 of the base 55. In FIG. 7, the condom 10 has been removed from on top of the dome portion 59 and the seal 80 is in the process of being removed from the adhesive opening 85 to allow access to the adhesive remover R within the adhesive remover cavity 75.

As shown in FIGS. 8-10, the condom 10 is depicted in various stages of application and use on the head H of the penis. As shown in FIGS. 8 and 9, the condom 10 is placed over at least a portion of the head H of the penis 90 so that the reservoir 30 is generally aligned with the urethra opening U, thereby allowing the reservoir 30 to collect the bodily fluids ejected through the urethra opening U. As shown in FIG. 10, once sexual intercourse is complete, the user can deliver the adhesive remover R by squeezing the edges of the individual disposable condom package 62 from which the seal 80 has been removed, thereby pushing the adhesive remover R from the adhesive remover cavity 75, through the adhesive opening 85, and onto or underneath the condom 10. For example, the user can lift the proximal end 14 of the condom 10 and deliver the adhesive remover R under the rim 40 of the condom 10. The user can then massage the adhesive remover R under the condom 10 to allow it to come into contact with the adhesive 20, thereby allowing the condom 10 to be detached and removed from the head H of the penis 90.

Figure 11A:
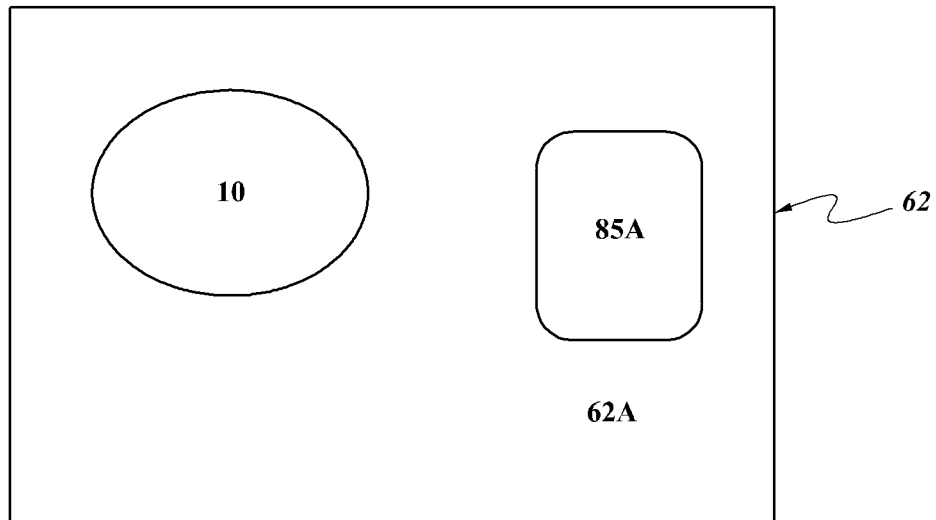
FIG. 11A shows an individual disposable condom kit, according to an exemplary embodiment.
Figure 11B:
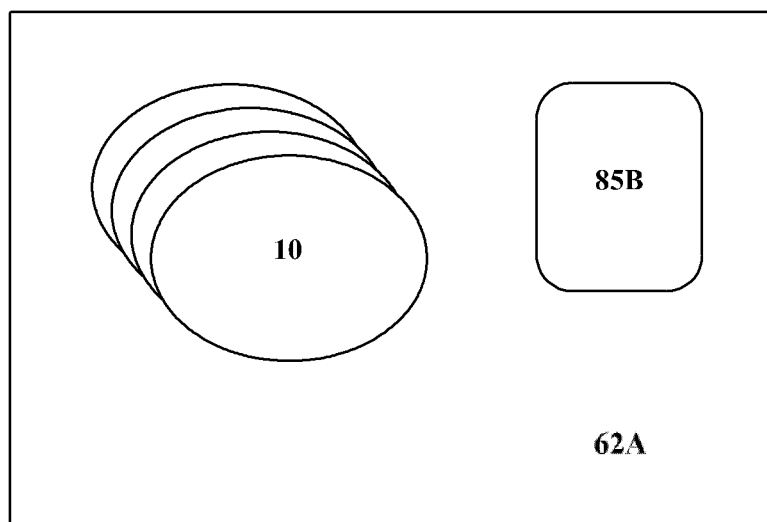
FIG. 11B shows a kit having a plurality of the condoms of FIG. 1, according to another exemplary embodiment.

As shown in FIG. 11A, an alternative individual disposable condom package 62 does not include the stacked arrangement of the dome portion 59 and the condom 10. Rather, the individual disposable condom package 62 includes a container 62A (e.g., a box, wrapper) containing a condom 10 (which can be wrapped, for example, in a plastic cover, wrapper, or packaging) and an adhesive remover package 85A separate from the condom 10 (e.g., such that the condom 10 and the adhesive remover R are co-packaged but separately packaged). In one embodiment, the adhesive remover package 85A includes the adhesive remover R like described above. In another embodiment, the adhesive remover package 85A includes a wipe contained inside a wrapper. Such a wipe could similarly be disposed within the adhesive remover cavity 75 described above. During use, following sexual intercourse, the user can tear the wrapper to remove the wipe and apply the wipe under the edge (e.g., rim 40) of the condom 10 to apply the adhesive remover R to the adhesive 20 to allow the condom 10 to be detached and removed from the head H of the penis 90.

As shown in FIG. 111B, an alternative kit does not include the stacked arrangement of the dome portion 59 and the condom 10. Rather, the kit includes the container 62A that includes a plurality of individually wrapped condoms 10 and an adhesive remover package 85B separate from the condoms 10. In one embodiment, the adhesive remover package 85B is or includes a set of individually wrapped wipes. During use, following sexual intercourse, the user can tear the wrapper off one of the wipes and apply the wipe under the edge (e.g., rim 40) of the condom 10 to apply the adhesive remover R to the adhesive 20 to allow the condom 10 to be detached and removed from the penis 90. In another embodiment, the adhesive remover package 85B is a container housing sufficient adhesive remover R for multiple applications (e.g., corresponding to the amount needed to remove the number of condoms 10 in the kit following their use) in spray or gel form. During use, following sexual intercourse, the user can deliver the adhesive remover R from the container (e.g., spray under the rim 40 of the condom 10, apply adhesive remover gel under the rim 40 of the condom 10, etc.) to apply the adhesive remover R to the adhesive 20 to allow the condom 10 to be detached and removed from the penis 90.

In an alternative embodiment, a plurality of the condoms 10 can be packaged in disposable sheets (e.g., like stickers) where, for example, the condoms 10 are adhesively coupled to the disposable sheet (e.g., along the base 55, over the dome portions 59, etc.) using the adhesive 20, with the non-adhesive side upward facing so a user can remove (i.e., peel) a respective one of the plurality of condoms 10 off of the sheet, exposing the adhesive 20 for application to the head H of the penis 90.

According to an exemplary embodiment, the condom 10 is manufactured or constructed from a material suitable for contact with the epidermis. For example, the condom 10 may be made of a material currently used to make condoms (e.g., latex, polyurethane, polyisoprene, lamb intestine, etc.). In some embodiments, the rim 40 at the proximal end 14 of the condom 10 is manufactured from a different material than the rest of the condom 10. By way of example, the rim 40 may be manufactured from a harder material (e.g., plastic, etc.). The rim 40 may not include the adhesive 20 such that the rim 40 can be easily grasped and lifted to facilitate removal of the condom 10 from the head H of the penis 90.

In some embodiments, the condom 10 is manufactured or constructed from a material capable of dissolving (e.g., a dissolvable material, polyvinyl alcohol, solvent soluble polymer, etc.). In such embodiments, the condom 10 may be capable of dissolving such that removing the condom 10 from the penis 90 may include dissolving the condom 10 (e.g., following use in sexual intercourse). By way of example, the condom 10 can be exposed to a dissolving agent (e.g., a liquid, gel, spray, etc.) or water of a predetermined temperature, thereby initiating, facilitating, or causing the dissolving of the condom 10. In one embodiment, where water of a predetermined temperature is used to dissolve the condom 10, hot water at a temperature above the standard body temperature or temperature of various human orifices (e.g., mouth, vagina, rectum, etc.) may be used to dissolve the condom 10, such as water at or above 101 degrees F., at or above 102 degrees F., at or above 103 degrees F., at or above 105 degrees F., at or above 107 degrees F., etc. (e.g., hot water in a shower, in a bathtub, from a sink, etc.). In other embodiments, the adhesive 20 of the condom 10 is a water or solvent soluble agent (e.g., thermoplastic adhesive, such as Aquabond 55, 65, 85) to dissolve the condom material.

The condom 10 can be constructed in a concave shape, like that of a dome, to be fitted to the head H of the penis 90. The condom 10 may be manufactured in various different sizes to accommodate varying sized penises 90 or to surround more or less of the head H of the penis 90 (e.g., only a portion of the head H, the entire head H but not the shaft S, etc.). As discussed above, the condom 10 may include the reservoir 30 at the apex or tip of the concave hull/body of the condom 10 (e.g., the innermost area of the outer convex surface 18a of the condom 10). The reservoir 30 can be positioned directly over the urethra opening U when the condom 10 is applied to the head H of the penis 90 to hold, contain, and prevent the escape of fluids (e.g., semen) out of the condom 10. The material of the condom 10 may be elastic and expand to contain the fluids that are ejaculated from the urethra opening U of the penis 90. According to an exemplary embodiment, the condom 10 is disposable and for single use.

The condom 10 may include the adhesive 20 (e.g., an epidermal adhesive, etc.) applied to at least a portion of the inner concave surface 18b of the condom 10 (i.e., applied on the concave side of the condom 10 that contacts with the skin of the head H of the penis 90).

According to an exemplary embodiment, the adhesive 20 is not applied to the reservoir 30 or the immediately surrounding portions of the inner concave surface 18b. Therefore, the adhesive 20 may be applied to cover the full area of the inner concave surface 18b excluding the area that is positioned directly over the urethra opening U (i.e., the reservoir 30 and area directly surrounding the reservoir 30). The adhesive 20 may be a commercially available topical skin adhesive approved for use on the epidermis (e.g., spirit gum adhesive, mastisol, Torobot cement glue, Skin-Tack liquid adhesive, Osto Bond skin bonding latex adhesive, Uro-Bond III 5000 Silicone Skin Adhesive, etc.).

In one embodiment, the adhesive 20 preferably inhibits (e.g., limits, prevents, etc.) irritation on the epidermis. In a preferred embodiment, the adhesive 20 is not applied to one side (i.e., the top side, the convex side) of the condom 10. In some embodiments, the adhesive 20 can form a ring around the lowermost area of the condom 10. In some embodiments, the adhesive 20 is activated upon contact with air (e.g., when the condom 10 is removed from the individual disposable condom package 62, when the condom 10 is removed from its wrapper, etc.). In one embodiment, the condom 10 is secured to the head H of the penis 90 with the adhesive 20 on one side. In another embodiment, the condom 10 is secured to the head H of the penis 90 without use of the adhesive 20 (e.g., a "stretch fit" design, a "tensioned" design, etc.). According to an exemplary embodiment, the condom 10 and/or the adhesive 20 inhibit (e.g., prevent, capture, etc.) fluids ejaculated from the urethra opening U from escaping the condom 10. In some embodiments, the adhesive 20 or the reservoir 30 includes a spermicide (e.g., to kill sperm ejaculated from the urethra opening U during intercourse).

The adhesive removal agent R may be one of many commercially available removal agents that correspond to deactivate the adhesive 20 (e.g., Smith & Nephew Uni Solve Adhesive Remover, Skin-Tac-H Adhesive TacAway Remover, Detachol Adhesive Remover, etc.). The adhesive remover R can be in one of multiple commercially available forms (e.g., wipes, gels, sprays, etc.). The adhesive remover R can be applied topically under or over the condom 10 to deactivate the adhesive bond of the adhesive 20. By way of example, the adhesive remover R may be massaged under or over the condom 10 for a period of time (e.g., 1-45 seconds, etc.) to deactivate the adhesive bond.

Figure 13:
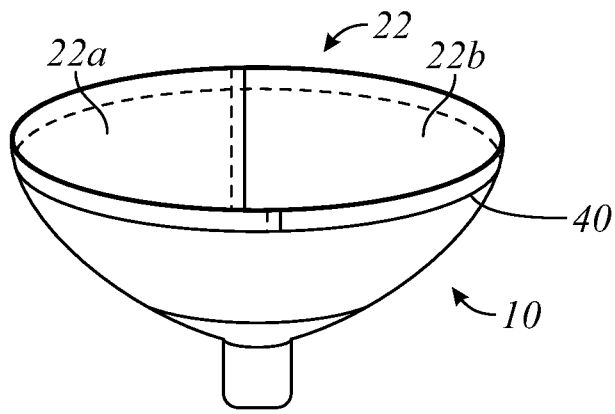
FIGS. 13 and 14 are schematic perspective bottom views and FIG. 15 is a planar bottom view showing a protective sheeting over a portion of the condom of FIG. 1 prior to use and the removal of the protective sheeting, according to an exemplary embodiment.
Figure 14:
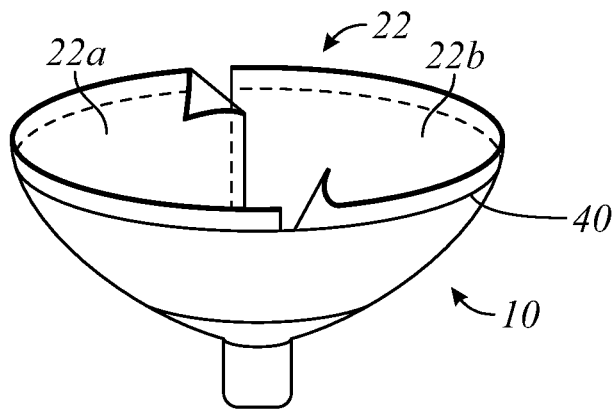

In some embodiments, as shown in FIGS. 13 and 14, the condom 10 includes a removable lining (e.g., sheet, film, liner, etc.), shown as cover 22, that is removably attached to the underside (i.e., the inner concave surface 18b) of the condom 10 to protect the adhesive 20 disposed thereunder from dust and other contaminants. The adhesive 20 may be a pressure sensitive adhesive including an acrylic, cyanoacrylate, silicone, polyurethane, etc. The adhesive 20 may have a similar bond strength to high-strength waterproof Band-Aid adhesive bandages (e.g., "Band-Aid Water Blocker Plus"). The cover 22 can be removed when desired by the user to expose the adhesive 20 applied to the inner concave surface 18b of condom 10. The adhesive 20 of the condom 10 is, therefore, protected by the cover 22 until the user is ready to remove the cover 22 and apply the condom 10. The cover 22 may be manufactured from a paper, plastic, or film material. In some embodiments, the condoms 10 having the cover 22 may be packaged in a stacked arrangement (e.g., the cover 22 prevents the adhesive 20 on a first, upper condom 10 from sticking to a second, lower condom 10 in the stack, etc.).

In some embodiments, the cover 22 is a single, continuous piece. In other embodiments, the cover 22 includes two or more pieces. As shown in FIGS. 13 and 14, the cover 22 includes a two-piece structure including a first piece 22a and a second piece 22b that are removably coupled to portions of the inner concave surface 18b of the condom 10. In one embodiment, the first piece 22a and the second piece 22b at least partially overlap (e.g., one of the two pieces may be larger than the other of the two pieces). By way of example, the first piece 22a may at least partially overlay the second piece 22b. The adhesive 20 may not be located at the overlay portion such that the user can easily start the removable process by pulling on the first piece 22a. The first piece 22a and the second piece 22b may fit along the three dimensional curvature of the inner concave surface 18b of the condom 10 such that the cover 22 may be domed shaped and fitted to the interior portion of the condom 10. The first piece 22a and the second piece 22b may overlap at the mid-point of the underside of the condom 10 such that the first piece 22a is removed starting from the mid-point of the condom 10.

Figure 15:
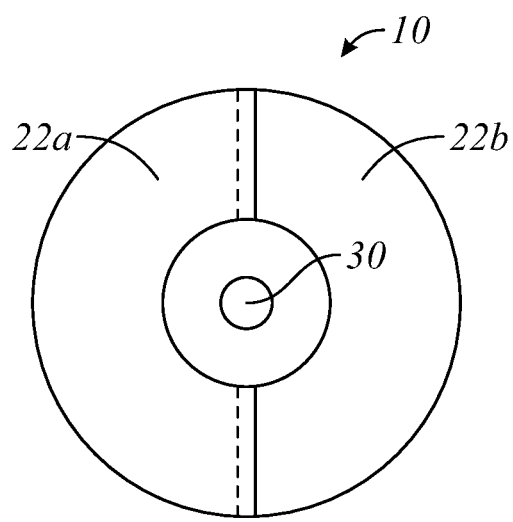

As shown in FIGS. 13 and 14, the cover 22 or the first piece 22a and the second piece 22b have a length or are arranged such that a portion thereof extends beyond the rim 40 at the proximal end 14 of the condom 10. Such an extended portion may allowed for easier removability of the cover 22 from the condom 10 by pulling from the portion thereof that extends beyond the proximal end 14 of the condom 10. As shown in FIG. 15, the cover 22 or the first piece 22a and the second piece 22b of the cover 22 at least partially cover the interior portion of the condom 10 (e.g., ⅔ of the area of the interior portion of the condom 10, at least the portion where the adhesive 20 is located, etc.). In some embodiments, the cover 22 extends along the entirety of the interior surface of the condom 10. In some embodiments, the cover 22 does not extend across the reservoir 30 and/or the surrounding area (e.g., where the adhesive 20 is not located). In an alternative embodiment, the cover 22 extends across and is coupled to the rim 40 at the proximal end 14 of the condom 10 and lays flat or is slightly concave such that the cover 22 seals the adhesive 20 within the interior of the condom 10 without touching and directly covering the adhesive 20 located on the interior of condom 10 (e.g., the cover 22 functions like a lid to the condom 10).

Figures 16, 17:
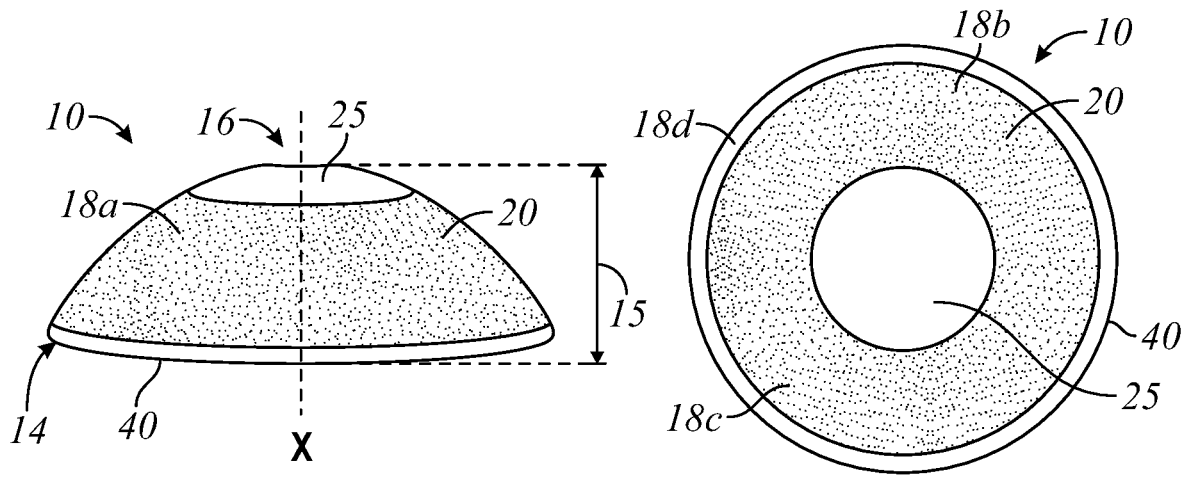
FIG. 16 is a top perspective view of a condom, according to another exemplary embodiment.
FIG. 17 is a bottom view of the condom of FIG. 16, according to an exemplary embodiment.
Figure 18:
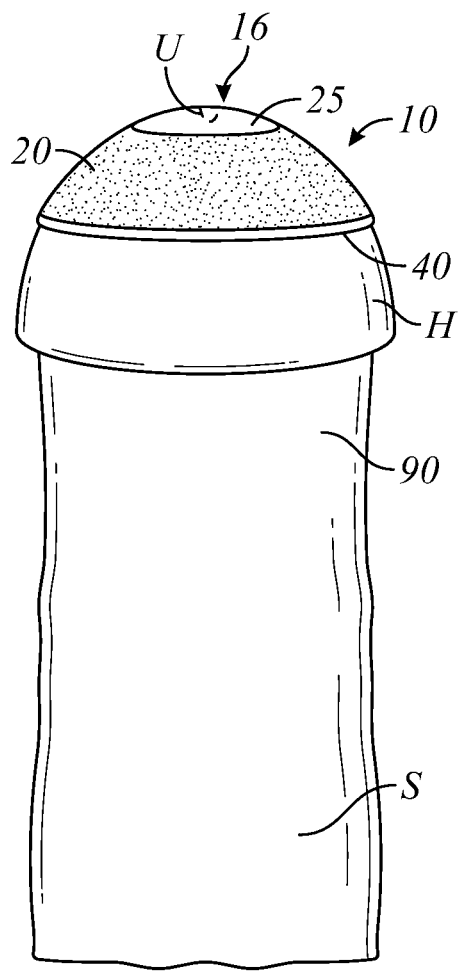
FIG. 18 shows the condom of FIG. 16 in place on a head of a penis, according to an exemplary embodiment.

As shown in FIGS. 16-18, the condom 10 does not include the reservoir 30 positioned at the distal end 16 of the condom 10. In such an embodiment, the circumferential gap 25 without the adhesive 20 may be configured to expand or otherwise deform to contain the fluids that are ejaculated from the urethra opening U of the penis 90. In one embodiment, the portion of the condom 10 associated with the circumferential gap 25 is manufactured from a first material having a first flexibility or elasticity and the portion 18c of the condom 10 having the adhesive 20 disposed thereon is manufactured from a second material having a second flexibility or elasticity that is less than the first flexibility or elasticity (e.g., the portion 18c is more rigid).

Further, in some embodiments, the portion 18c that has the adhesive disposed thereon extends to the rim 40 at the proximal end 14 of the condom 10 (i.e., the ring 18d without the adhesive 20 is not present). In such embodiments, the adhesive 20 may extend from the rim 40 at least partially up the inner concave surface 18b and cover between 1% to 50% of the area of the inner concave surface 18b, thereby forming an adhesive strip around the lower portion of the condom 10. In one embodiment, the portion of the condom 10 associated with the circumferential gap 25 is larger or has a different shape (e.g., has a balloon shape, etc.) than the portion 18c with the adhesive 20 disposed thereon such that the portion associated with the circumferential gap 25 (with or without the reservoir 30) may collect a greater quantity of fluids ejaculated from the urethra opening U. It should be understood that the disclosure herein regarding the condom 10 shown in FIGS. 1-15 (other than the reservoir 30) may similarly apply to the condom 10 shown in FIGS. 16-18.

Figures 19, 20:
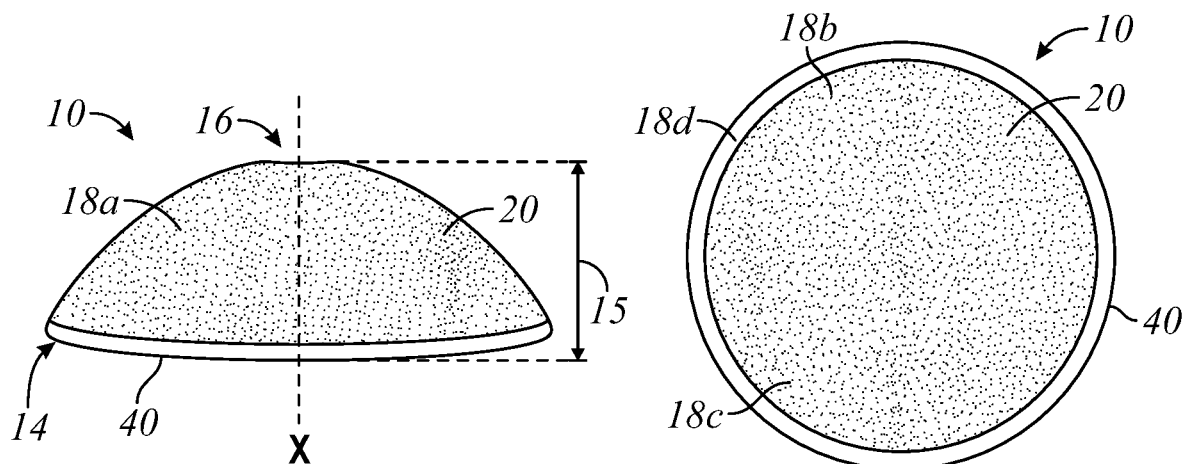
FIG. 19 is a top perspective view of a condom, according to still another exemplary embodiment.
FIG. 20 is a bottom view of the condom of FIG. 19, according to an exemplary embodiment.
Figure 21:
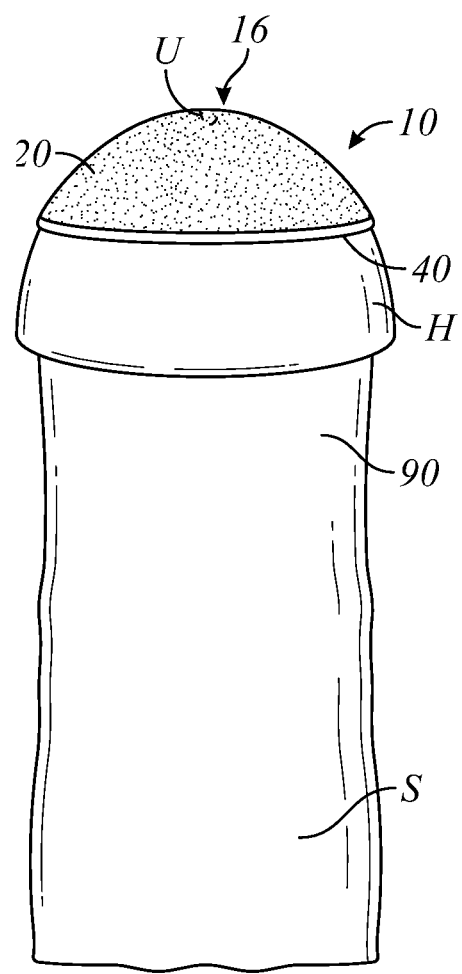
FIG. 21 shows the condom of FIG. 19 in place on a head of a penis, according to an exemplary embodiment.

As shown in FIGS. 19-21, the condom 10 does not include the reservoir 30 or the circumferential gap 25 positioned at the distal end 16 of the condom 10. In such an embodiment, the adhesive 20 may extend along the entirety of the inner concave surface 18b of the condom 10, including or excluding the ring 18d at the proximal end 14 of the condom 10.

The adhesive 20 at the distal end 16 may be configured to seal (e.g., temporarily) the urethra opening U (e.g., to slow the speed and reduce the force at which fluids are ejaculated from the urethra opening U during an ejaculation event). It should be understood that the disclosure herein regarding the condom 10 shown in FIGS. 1-18 (other than the reservoir 30 and the circumferential gap 25) may similarly apply to the condom 10 shown in FIGS. 19-21.

As shown in FIGS. 22-24, the condom 10 does not include the adhesive 20. Rather, the rim 40 at the proximal end 14 of the condom 10 is or includes an elastic tensioning element, shown as tension band 42. In one embodiment, the condom 10 with the tension band 42 includes the reservoir 30 at the distal end 16 thereof. In another embodiment, the condom 10 with the tension band 42 does not include the reservoir 30 at the distal end 16 thereof. In such an embodiment, the distal end 16 of the condom 10 may be configured to expand or otherwise deform to contain the fluids that are ejaculated from the urethra opening U of the penis 90.

As shown in FIG. 24, the condom 10 is sized to surround the entire head H of the penis 90. To facilitate covering the entire head H of the penis 90, the height 15 between the proximal end 14 and the distal end 16 of the condom 10 may correspond to the size of the head H of the penis 90 (e.g., the condom 10 is manufactured at various sizes to fit various sized penis heads).

Alternatively, the condom 10 may be manufactured from a material that allows the condom 10 to stretch over the entire head H of the penis 90 to accommodate a range of penis head sizes.

According to the exemplary embodiment shown in FIG. 24, the tension band 42 is configured to engage with the penis 90 at a base B of the head H of the penis 90 (e.g., the rim of the head H, the neck of the penis 90, the portion of the head H that meets the shaft S and that extends radially outward from the shaft S, etc.). The tension band 42 may be configured to constrict or tighten the rim 40 of the condom 10 around the shaft S at the base B of the head H of the penis 90 to contain the fluids that are ejaculated from the urethra opening U of the penis 90. The condom 10 may, therefore, provide a "stretch fit" or a "tensioned fit" over the head H of the penis 90.

In another embodiment, the condom 10 having the tension band 42 is sized to cover only a portion of the head H of the penis 90. In such an embodiment, the entire condom 10 (including or excluding the reservoir 30, if the condom 10 includes the reservoir 30) may be manufactured from an elastic material that permits the condom 10 to stretch around and then squeeze the portion of the head H of the penis 90 to secure the condom 10 to the head H. By way of example, the condom 10 may be applied to the head H of the penis 90 by placing one side of the rim 40 along one side of the head H of the penis 90 (e.g., a side of the head H parallel to the length direction of the natural opening of the urethra opening U), holding the one side of the rim 40 with one hand, grabbing the opposing side of the rim 40 with the other hand, stretching the condom 10 over the urethra opening U to the opposing side of the head H, and releasing the rim 40 such that (i) the opposing side of the rim 40 engages with the opposing side of the head H and (ii) the condom 10 squeezes the portion of the head H. In such an embodiment, the condom 10 may apply a radially inward force that produces a sufficient frictional force against the head H of the penis 90 to limit movement of the condom 10 during use and keep the condom 10 secured to the head H of the penis 90. In some embodiments, the radially inward force provided by the condom 10 is sufficient to at least partially close the urethra opening U (e.g., to slow the speed and reduce the force at which fluids are ejaculated from the urethra opening U during an ejaculation event).

In some embodiments, the condom 10 of FIGS. 22-24 that provides the "stretch fit" or "tensioned fit" additionally includes the adhesive 20 along at least the portion 18c and/or the ring 18d to further secure the condom 10 to the head H of the penis 90. The adhesive 20 may additionally be positioned over the urethra opening U to further close the urethra opening U.

Figure 12:
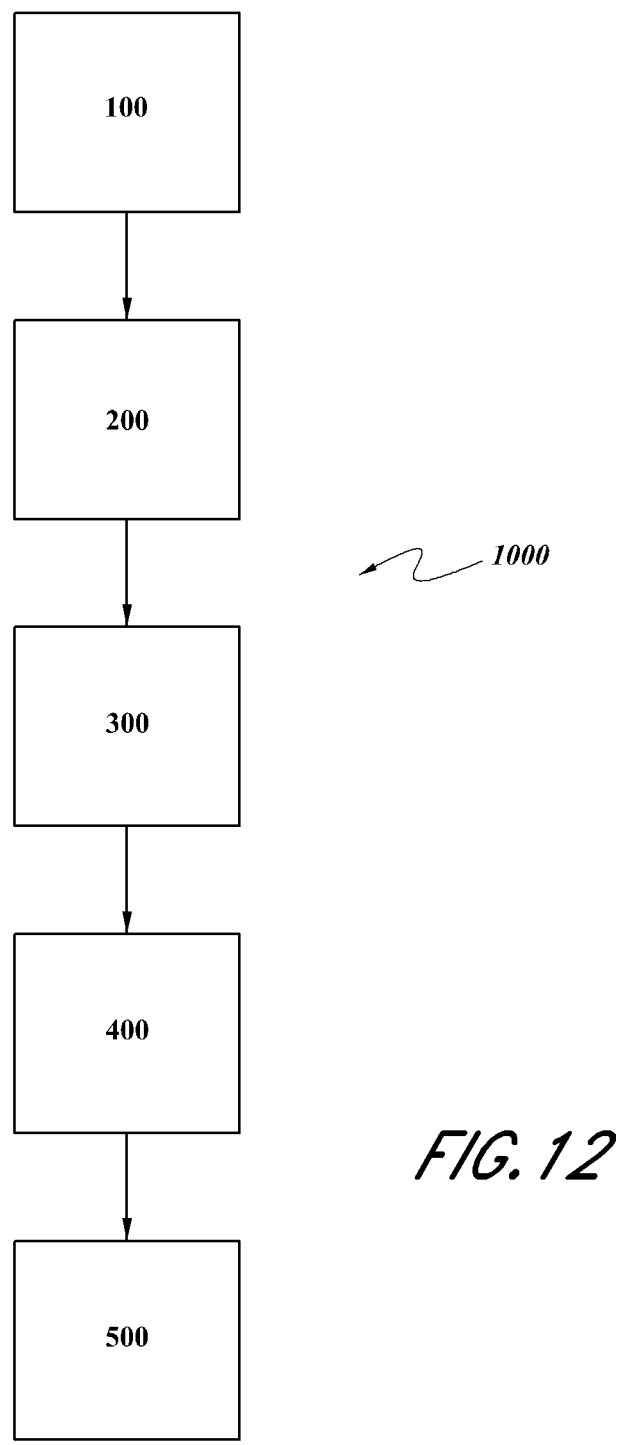
FIG. 12 shows a block diagram depicting a method of using a condom, according to an exemplary embodiment.

FIG. 12 shows a block diagram for a method 1000 of using a condom product or kit (e.g., the condom products and kits shown in FIGS. 1-11B and 13-24). The method 1000 includes step 100, step 200, step 300, step 400, and step 500. Step 100 includes opening a package (e.g., the individual disposable condom package 62, the container 62A and the individually wrapped condom 10, etc.). Step 200 includes removing a condom (e.g., the condom 10) from the package and placing the condom over the user's penis such that the condom adheres (e.g., with the adhesive 20) and/or secures (e.g., with a stretch fit) to at least a portion of the head of the penis. Step 300 includes optionally delivering adhesive remover (e.g., adhesive remover R, gel adhesive remover, spray adhesive remover, adhesive remover on a wipe, etc.) over and/or under at least a portion (e.g., the ring 18d, the rim 40, etc.) of the condom following sexual intercourse (e.g., if the condom is adhered to the head of the penis with adhesive, the adhesive remover may be used, otherwise if the condom is otherwise secured to the penis (without using adhesive) the adhesive remover may not be used). Step 400 includes optionally massaging the adhesive remover over and/or under the condom to bring the adhesive remover into contact with adhesive on a bottom surface of the condom (e.g., if adhesive is used to adhere the condom to the head of the penis). Step 500 includes removing the condom from the head H of the penis 90 for disposal. Steps 300 and 400 may be replaced with running the condom under water (e.g., water at a temperature above the standard body temperature or temperature of various human orifices, such that the condom dissolves, etc.). In some embodiments, steps 300 and 400 may be skipped even if the condom is adhered to the head of the penis with adhesive.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Language such as the phrases "at least one of X, Y, and Z" and "at least one of X, Y, or Z," unless specifically stated otherwise, is understood to convey that an element may be either X; Y; Z; X and Y; X and Z; Y and Z; or X, Y, and Z (i.e., any combination of X, Y, and Z). Thus, such language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the condom 10, the sheet package 50, the individual disposable condom package 62, and the container 62A as shown in the various exemplary embodiments is illustrative only. Additionally, any element disclosed in one embodiment may be incorporated or utilized with any other embodiment disclosed herein.

The invention claimed is:

1. A condom product comprising:
 a condom including:
  a body having an interior surface, an exterior surface, a distal end, and a proximal end having a peripheral edge;
  an adhesive disposed along at least a portion of the interior surface, the adhesive configured to removably adhere the body to a penis;
 wherein the condom is sized such that the interior surface is configured to extend along at least a portion of a head of the penis, but not along a shaft of the penis; and
 wherein the condom is dissolvable when exposed to a fluid above standard body temperature.

2. The condom product of claim 1, further comprising an adhesive remover.

3. The condom product of claim 2, wherein the condom is stored in a first package and the adhesive remover is stored in a second package, further comprising a container that co-packages the first package and the second package.

4. The condom product of claim 3, wherein the container co-packages a plurality of the first packages and one or more of the second packages.

5. The condom product of claim 2, further comprising a package including:
 a base;

an adhesive remover reservoir disposed along the base, wherein the adhesive remover is stored within the adhesive remover reservoir, and wherein the condom is stacked on top of the adhesive remover reservoir; and
a removable cover coupled to the base and extending over the adhesive remover reservoir and the condom.

6. The condom product of claim 1, wherein the adhesive is not positioned at the distal end.

7. The condom product of claim 6, wherein the distal end comprises a first material having a first flexibility or elasticity and the portion having the adhesive disposed thereon comprises as a second material having a second flexibility or elasticity that is less than the first flexibility or elasticity.

8. The condom product claim 1, wherein the condom includes an elastic band positioned at the peripheral edge, the elastic band configured to at least partially secure the condom to the head of the penis.

9. The condom product of claim 8, wherein the condom is sized such that the elastic band is configured to engage with a base of the head of the penis.

10. The condom product of claim 1, wherein the condom is dissolvable when exposed to a fluid at or above a threshold temperature.

11. The condom product of claim 10, wherein the fluid is water at a temperature above the standard body temperature.

12. The condom product of claim 1, further comprising:
an adhesive remover configured to be applied to the urethra condom to deactivate the adhesive to facilitate removal of the urethra condom from the head of the penis; and
a package removably housing the urethra condom and the adhesive remover.

13. The condom product of claim 12, wherein the package includes:
a base;
an adhesive remover reservoir positioned along the base, wherein the adhesive remover is stored within the adhesive remover reservoir, and wherein the condom is stacked on top of the adhesive remover reservoir; and
a removable cover coupled to the base and extending over the adhesive remover reservoir and the condom.

14. The condom product of claim 1, wherein the adhesive is positioned at the distal end, and wherein the adhesive at the distal end is configured to at least partially close a urethra opening of the penis.

15. The condom product of claim 1, wherein the adhesive is not positioned proximate the peripheral edge, thereby defining a ring that does not include the adhesive along the interior surface adjacent the peripheral edge.

16. The condom product of claim 1, wherein the adhesive is positioned proximate the peripheral edge and extends at least partially along the interior surface toward the distal end to define an adhesive strip around at least a lower portion of the interior surface proximate the proximal end.

17. The condom product of claim 1, wherein the condom includes a removable liner disposed over at least the portion of the interior surface having the adhesive disposed thereon.

18. The condom product of claim 1, wherein the body comprises a material that permits the body to stretch around and squeeze against the portion of the head of the penis to (i) at least partially secure the condom to the head of the penis and (ii) at least partially close a urethra opening of the penis.

* * * * *